United States Patent
Cinquin et al.

(10) Patent No.: US 6,385,475 B1
(45) Date of Patent: May 7, 2002

(54) PROCESS AND DEVICE FOR THE PREOPERATIVE DETERMINATION OF THE POSITIONING DATA OF ENDOPROSTHETIC PARTS

(76) Inventors: Philippe Cinquin, 15, chemien de la Bastille, F-38700 La Tronche; Stephane Lavallee, rue de la Combe d'Alloix, F-38660 Saint Vincent-de-Mercuze; Francois Leitner, L'Oree du Parc, F-38410 Uriage; Richard Minfelde, 48, rue Raymond de Temple, F-94300 Vincennes, all of (FR); Frederic Picard, 263 Hoodridge Dr. Mount Lebanon, Pittsburgh, PA (US) 15234; Dominique Saragaglia, 3 allee du Joanny, F-38640 Claix (FR); Hans-Joachim Schulz, Brunnentalstrasse 98, D-78532 Tuttlingen (DE)

( * ) Notice: Subject to any disclaimer, the term of this patent is extended or adjusted under 35 U.S.C. 154(b) by 0 days.

(21) Appl. No.: 09/389,315

(22) Filed: Sep. 2, 1999

Related U.S. Application Data

(63) Continuation of application No. PCT/EP98/00399, filed on Jan. 24, 1998.

(30) Foreign Application Priority Data

Mar. 11, 1997 (DE) .......................................... 197 09 960

(51) Int. Cl.$^7$ ................................................. A61B 5/00
(52) U.S. Cl. ........................ 600/407; 606/130; 128/920
(58) Field of Search .................................. 600/407, 595, 600/473, 425, 426; 606/130, 79, 82, 87, 88, 99, 102; 348/77; 128/920

(56) References Cited

U.S. PATENT DOCUMENTS 4,631,676 A * 12/1986 Pugh
4,841,975 A * 6/1989 Woolson (List continued on next page.)

FOREIGN PATENT DOCUMENTS

EP          0 322 363          6/1989

OTHER PUBLICATIONS

Orti, Rachael et al., "Computer Assisted Knee Ligament Reconstruction," Medical Informatics, Ethics, Cardiology, Instrumentation, San Diego, Oct. 28–31, 1993, pp. 936–937.

(List continued on next page.)

*Primary Examiner*—Marvin M. Lateef
*Assistant Examiner*—Shawna J. Shaw
(74) *Attorney, Agent, or Firm*—Barry R. Lipsitz; Douglas M. McAllister

(57) ABSTRACT

In order to be able to ascertain the position of the bone in the body without complicated procedures in a process for the preoperative determination of the positioning data of endoprosthetic parts of a central joint relative to the bones forming the central joint, a respective outer articular point is determined by way of movement of the bones about a respective outer joint which is located at the end of the two bones facing away from the central joint. An articular point is determined for each of the two bones in the area of the central joint, and a direction characteristic for each of these bones is determined by way of a straight-line connection of the two articular points obtained in this manner for the two bones. The orientation of the endoprosthetic parts relative to this characteristic direction is then determined. Apparatus for carrying out the process is also provided.

60 Claims, 3 Drawing Sheets

U.S. PATENT DOCUMENTS

| | | | | |
|---|---|---|---|---|
| 4,938,762 A | * | 7/1990 | Wehrli | 606/88 |
| 4,979,949 A | * | 12/1990 | Matsen, III et al. | 606/53 |
| 5,007,912 A | * | 4/1991 | Albrektsson et al. | 606/87 |
| 5,249,581 A | | 10/1993 | Horbal et al. | |
| 5,611,353 A | * | 3/1997 | Dance et al. | |
| 5,676,157 A | * | 10/1997 | Kramer | |
| 5,748,767 A | * | 5/1998 | Raab | 382/128 |
| 5,871,018 A | * | 2/1999 | Delp et al. | |
| 6,167,145 A | * | 12/2000 | Foley et al. | 382/128 |
| 6,217,582 B1 | * | 4/2001 | Slocum | 606/87 |

OTHER PUBLICATIONS

Kienzle, T.C. et al., "An Integrated CAD–Robotics System for Total Knee Replacement Surgery," Proceedings of the International Conference on Robotics and Automation, Atlanta, May 2–6, 1993, vol. 1, May 3, 1993, pp. 889–894.

Fadda, M. et al., "Computer–Assisted Knee Arthroplasty at Rizzoli Institutes," IN MRCAS 94, Medical Robotics and Computer Assisted Surgery, Pittsburgh, 1994, pp. 26–31.

Kienzle, T.C. et al., "A Computer–Assisted Total Knee Replacement Surgical System Using a Calibrated Robot," MIT Press, Cambridge, MA, 1996, pp. 409–416.

* cited by examiner

PROCESS AND DEVICE FOR THE PREOPERATIVE DETERMINATION OF THE POSITIONING DATA OF ENDOPROSTHETIC PARTS

This application is a continuation of international application number PCT/EP98/00399, filed Jan. 24, 1998.

The invention relates to a process for the preoperative determination of the positioning data of endoprosthetic parts of a central joint relative to the bones forming the central joint. Moreover, the invention relates to a device for carrying out this process.

BACKGROUND OF THE INVENTION

In the case of surgical operations, with which joints between two bones have to be replaced by endoprostheses, it is extremely important for the endoprosthetic parts to be positioned exactly relative to the bones; deviations in the order of magnitude of more than 2° already call into question the success of such an operation.

It is known, for the preparation of surgical operations, to determine the position of bones in the body and the relative positioning of the bones bordering on the joint to be replaced by means of various processes in order to be able to plan prior to the operation how the endoprosthetic parts have to be inserted relative to the bones. For example, it is known to determine the outer contour of the bones bordering on the joint to be replaced by means of computer tomography scans; on the basis of the data thus gained sets of data may be compiled which correspond to the outer contours of the bones and which can then be used for planning the orientation of the prosthetic parts (M. Fadda et al "Computer-Assisted Knee Arthoplasty at Rizzoli Institute"; MRCAS 94, Medical Robotics and Computer Assisted Surgery, Pittsburgh, 1994, pages 26 to 31; T. C. Kienzle III et al "A Computer-Assisted Total Knee Replacement Surgical System Using a Calibrated Robot", MIT Press, Cambridge, Mass., 1996, pages 409 to 416).

This presupposes a complicated examination of the patient prior to beginning the operation which often cannot be carried out at the actual place of operation and therefore, as a rule, also not at the same time as the operation. Moreover, the patient has to be subjected to a high dose of radiation; finally, expensive apparatus and equipment is required for this examination.

It is already known to compare the position of the bones with one another prior to and after the operation in that marking elements are secured to the bones and their position in the space can be determined by suitable camera-like devices (U.S. Pat. No. 5,249,581). The result of the operation can be checked with such a device as the surgeon can compare the orientation of the bones prior to and after the operation. It is not, however, possible with this process to determine the positioning data of the prosthetic parts to be inserted preoperatively; also with this process the position of the prosthetic parts on the bone must be determined preoperatively by, for example, the exact position of the bones in the body and their positioning relative to one another being determined by means of computer tomography scans.

SUMMARY OF THE INVENTION

The object of the invention is to specify a process, with which the position of the prosthetic parts relative to the bone can be determined preoperatively without complicated examination procedures of the patient being necessary for this purpose; in particular, CT scans or similar examination procedures are intended to be made superfluous.

This object is accomplished in accordance with the invention, in a process of the type described at the outset, in that a respective outer articular point is determined by way of movement of the bones about a respective outer joint which is located at the end of the two bones facing away from the central joint, that an articular point is determined for each of the two bones in the area of the central joint, that a direction characteristic for each of these bones is determined by way of a straight-line connection of the two articular points found in this manner for the two bones and that the orientation of the endoprosthetic parts relative to this characteristic direction is determined.

The process described may be used on all body parts, with which the bones determining the joint to be replaced are likewise connected at their other end to additional bones via a joint. In the following, the joint to be replaced is designated as "central joint", the joints adjoining on the outer sides as "outer joints". With the process described, the outer joints are used for the purpose of supplying preoperative information concerning the position of the bones adjoining the central joint. The bones coming together at the two outer joints are, namely, moved relative to one another, and as a result of this movement the position of the outer joints is determined, to be more exact articular points of considerable invariance. This becomes clear with the example of the leg although the process described can also be used on all other limbs, for which central and outer joints are present, for example, the arm.

In the case of the leg, the central joint is formed by the knee joint, the two outer joints by the hip joint and by the ankle. The hip joint is a ball joint and so the center point of this ball joint can be determined by way of movement of the thigh in relation to the hip joint, i.e. an articular point of greatest invariance, that is an articular point which is immovable during the movement of the two bones relative to one another.

In a similar manner, such a point of greatest invariance can also be determined for the ankle. In this case, the ankle is essentially a joint which facilitates only a pivoting about a transverse axis but a rotation about the longitudinal axis is also possible to a small extent and so a point can be determined as a result of the superposition of these two pivoting movements which remains essentially unmoved during every movement of the ankle.

In the area of the knee, articular points are determined, in addition, in a similar manner, wherein various methods can be available to the surgeon for this purpose.

When the knee joint is intact and still allows normal movements, the articular points close to the knee can also be determined by way of movement of the two adjoining bones about this joint. The knee joint does perform a relatively complicated rolling and sliding movement; nevertheless, points, with which the movement during the bending of the knee is minimal, may be determined during performance of this complicated, superposed movement and, moreover, during a rotation of the lower leg about the vertical axis; such a point of maximum invariance is defined as articular point.

In accordance with another embodiment of the invention, articular points can also be determined by these being established at the central joint by way of palpation of the joint surfaces. When replacing a central joint, i.e., for example, the knee joint, this area must be opened up in any case, and the surgeon can then establish particular, striking points of the joint surfaces, for example, intercondylar by touch. These are then specified as articular points.

It is also possible in another embodiment of the invention to determine the articular points of the bones at the central joint from a set of data which reproduces the contour of the joint surface at the central joint. This contour of the joint surface can be detected after the opening up of the knee joint, for example, by a scanner which is guided along the joint surface and which in various positions along the joint surface supplies signals corresponding to its position to a data processing system. This may determine the contour of the joint surface in this manner, and on the basis of this determined contour the surgeon can then establish which point will be used as articular point of the central joint.

As a result of this determination of the articular points in the two outer joints and in the central joint, characteristic directions may be determined for each of the two bones forming the central joint in that the two articular points of each bone are connected to one another in a straight line. These characteristic directions are then utilized for the orientation of the prosthetic parts, i.e. on the basis of this characteristic direction the inclination of the prosthetic parts, at which these are intended to be inserted into the bone, is determined.

For determining this characteristic direction it is not necessary to determine the bone in its entire contour beforehand, for example, by way of computer tomography but the articular points are, in the ideal case, determined exclusively by the kinematical determination of the articular points in the central joint and in the two outer joints. Only in the case, in which the central joint no longer allows such a determination due to damage will the described determination by way of palpation or by imaging the contour of the joint surface replace the kinematical determination. In any case, the determination of the position of the bone can take place immediately prior to the actual operation; it is not necessary to carry out complicated examinations some time prior to the operation.

In accordance with a preferred embodiment of the invention, it may be provided for sawing planes serving as contact surfaces for the endoprosthetic parts to be determined for the orientation of these parts, the sawing planes taking up a predetermined orientation relative to the characteristic direction; in particular, these sawing planes can be at right angles to the characteristic direction.

If such an orientation of the sawing planes, against which the prosthetic parts are placed, is selected, a course of the flexion axis of the central joint is obtained which is at right angles to the two characteristic directions of the two bones ending at the central joint, and this results in the characteristic directions of these two bones forming a straight line when the central joint is straightened. This is an ideal course for the mechanical strain on the limb, in particular, a leg, and this can be achieved merely on account of the described determination of the characteristic directions of the two bones and by a corresponding orientation of the prosthetic parts relative to these characteristic directions.

In addition to the prior determination of the inclination of such sawing planes relative to the characteristic distance, it may also be provided in a further, preferred embodiment for the sawing plane to be arranged at a specific distance from the articular point at the central joint determined for the respective bone. This results in a complete determination of the position and orientation of such a sawing plane on account of the kinematical determination of the articular points described above. However, this will not be practicable in every case since it is often not ascertained until during the operation to what extent a bone in the joint area is damaged, i.e. to what extent the bone has to be removed on the side of the joint. In these cases, it is sufficient when the inclination of the sawing plane relative to the characteristic direction is determined; the distance from the joint is then compensated for by a corresponding selection of different prosthetic parts of a set or by pads which are inserted between prosthetic part and bone. In this case, the surgeon has other possibilities of compensating for this space, where applicable.

In the simplest case, the kinematical determination of the position of the articular points is carried out by the surgeon by him moving the bones of the limb by hand relative to one another. It may, however, also be provided in a preferred embodiment for the movement of the bones for determining the articular points to be carried out by a drive device.

In a particularly preferred embodiment of the invention it is provided, for determining the articular points, for the two bones forming the central joint as well as the two bones adjoining the outer joints to each be securely connected to marking elements, the position of which is determined in the space by a measuring device which generates signals corresponding to this respective position and supplies these to a data processing system. The marking element and measuring devices may be ones such as those known per se from U.S. Pat. No. 5,249,581 but, in this case, it is of significance that not only the bones adjoining the central joint but also the two bones adjoining the outer joint are connected to marking elements of this type, i.e. that at least four bones with three included joints are present, wherein each bone bears such a marking element so that at least the articular points of the two outer joints can be determined during movement of the bones relative to these joints.

Radiation emitters or rather several radiation receivers, for example, infrared radiation emitters or ultrasound radiation emitters and corresponding receivers can, in particular, be used as marking elements and measuring device.

The marking elements may also be passive elements, for example, reflecting spheres, onto which radiation emitted by the measuring devices falls, this radiation being reflected from the spherical surface and then received again by the measuring device. It is merely essential for the measuring device to be able to determine the position of the marking elements in the space in a suitable manner.

In the data processing system, the point of the greatest invariance during the movement of the two bones forming the joint is then determined as articular point for each joint on the basis of the movement data.

The data thus obtained of a characteristic direction and, where applicable, of a sawing plane may be used in accordance with a preferred embodiment of the invention for the purpose of aligning a sawing jig relative to the characteristic direction of the bone. This alignment may, for example, be carried out by means of a robot which is controlled by the positioning data of the data processing system.

It is, however, also possible in accordance with a preferred embodiment of the invention for the alignment to be carried out manually and the orientation of the sawing jig relative to the characteristic direction to be thereby continuously determined as a result of measurement of the orientation of the jig. For preparing a saw cut, the surgeon need, therefore, only orient a corresponding jig such that this tallies with the calculated orientation of the sawing surface.

It is favorable when, for observing the deviation of the orientation of the sawing jig from the characteristic direction, difference signals are generated which are minimal during a correct orientation, and when these difference signals are indicated optically or acoustically. This enables the surgeon to align a sawing jig for the preparation of an operating step prior to the actual operation by observing these difference signals such that the orientation of the jig tallies with the orientation calculated for the sawing surface.

For example, the difference signals may be indicated by lines which are inclined relative to one another and extend parallel to one another with a correct orientation. In this respect, it is favorable when the lines intersect.

In another embodiment it may be provided for the difference signals to be indicated by the distance between two parallel lines, the distance between them disappearing with a correct orientation.

In another embodiment, the difference signals may be represented by tones having a varying loudness or varying frequency so that the surgeon can carry out the optimum orientation simply on the basis of the change in loudness or the change in frequency.

In this respect, it is favorable when two separate difference signals are generated for angular deviations in planes at right angles to one another so that it is possible for the surgeon without further ado to pivot the jig about angles which are vertical in relation to one another until the optimum position is found.

In principle, it is also possible, of course, to use the data of the characteristic direction obtained in this way directly for controlling a machining robot, i.e., for example, a sawing robot.

The object specified above is accomplished in accordance with the invention, in a device for the preoperative determination of the positioning data of endoprosthetic parts of a central joint relative to the bones forming the central joint with marking elements securable to the bones, a measuring device for determining the position of the marking elements in the space and with a data processing system, to which signals corresponding to the positioning data of the marking elements are supplied by the measuring device, in that at least one marking element is provided for each of the two bones forming the central joint as well as for each of the two bones adjoining these and connected to them via an outer joint.

This data processing system is designed in accordance with the invention such that it determines the points of greatest invariance as articular points from the signals during the movement of the bones about the two outer joints.

It is, furthermore, preferably provided for the data processing system to determine, in addition, the point of greatest invariance as articular point of the central joint from the signals during the movement of the bones about the central joint.

In accordance with a preferred embodiment, it is provided for a scanning instrument to be associated with the data processing system, this instrument supplying signals corresponding to its positioning to the data processing system. This scanning instrument may, for example, be used to identify a specific point on the joint surface of the opened joint and to pass on its position in the space to the data processing system. With this scanning instrument, a greater number of points can, furthermore, be determined on the joint surface and so the entire course of a scanned joint surface can be passed on to the data processing system which can determine from this a set of data, from which the entire course of the joint surface results. Finally, the scanning instrument may also be used to determine the course of the contact surface for a saw blade on orientation devices used, for example, sawing jigs.

The data processing system is designed such that it determines a characteristic direction for each bone from the position of the two articular points of the two bones adjoining the central joint.

In this respect, it is advantageous when the data processing system determines for the orientation of the endoprosthetic parts sawing planes serving as contact surfaces for them, these planes taking up a predetermined orientation relative to the characteristic direction, in particular, being at right angles to this characteristic direction.

In a further, preferred embodiment of the invention it is provided for it to comprise a drive device for the movement of the bones relative to the outer joints and, where applicable, for the movement relative to the central joint. As a result, the movement of the bones about the respective joints is carried out by machine and makes a fully automatic kinematical determination of the articular points possible.

The marking elements and the measuring device may be designed as radiation emitters and radiation receiver, respectively.

A robot may also be associated with the device, this robot aligning a tool jig or a tool relative to the characteristic direction.

It may, furthermore, be provided for a marking element to be associated with a tool or a tool jig, the orientation of this element being determined by the measuring device so that signals corresponding to this orientation are transferred to the data processing system. The data processing system thus receives not only the position signals of the bones but also the position signals of the tool or the tool jig and so the relative positioning can be monitored and, where applicable, controlled.

Further, preferred embodiments of the inventive device result from the subclaims.

The following description of preferred embodiments of the invention serves to explain the invention in greater detail in conjunction with the drawings. These show:

DETAILED DESCRIPTION OF THE INVENTION

Figure 1:
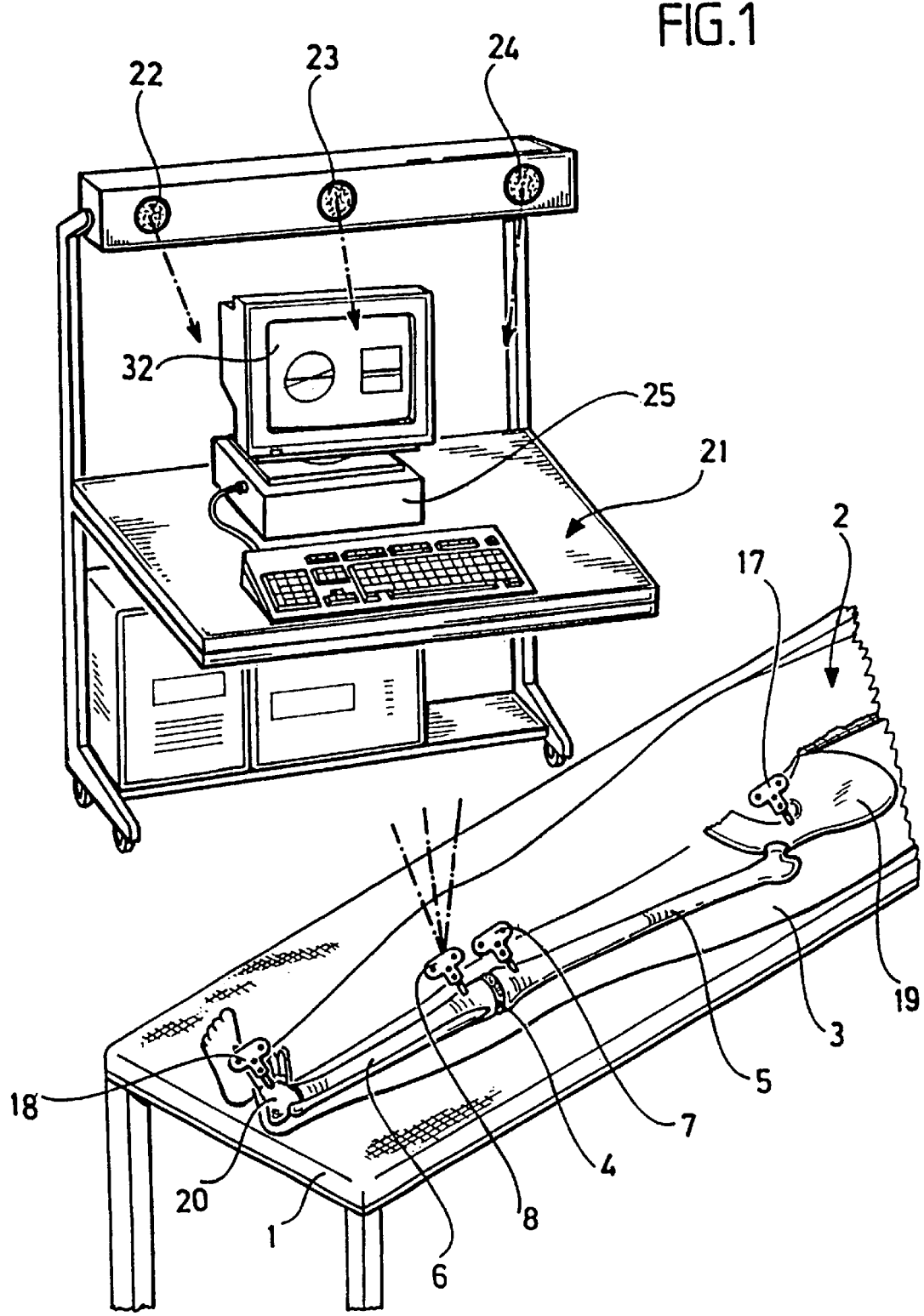
FIG. 1: a schematic view of a device for the determination of the characteristic direction of a thigh bone and a lower leg bone.

In FIG. 1, a patient 2, whose knee joint 4 in one leg 3 is to be replaced by an endoprosthesis, is illustrated schematically lying on an operating table 1.

In order to prepare this operation it is necessary to determine the orientation of the prosthetic parts to be used relative to the bones, i.e. relative to the thigh bone 5 and to the lower leg bone 6.

Figure 2:
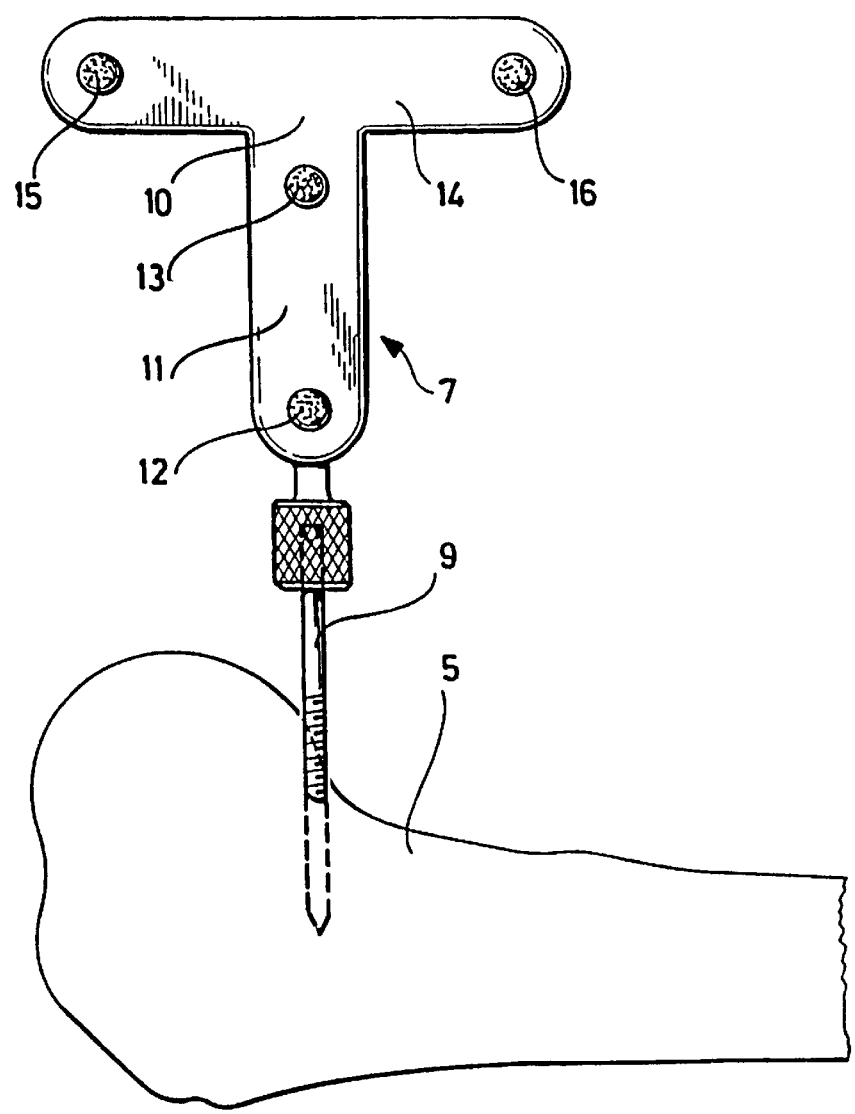
FIG. 2: a marking element inserted into a bone.

For this purpose, marking elements 7 and 8, respectively, are inserted not only into the thigh bone 5 but also into the lower leg bone 6 through small cuts made in the surrounding tissue, as illustrated in FIG. 2. These marking elements 7, 8 comprise a foot 9 in the form of a bone screw adapted to be screwed into the bone and a T-shaped attachment member 10 which bears two radiation emitters 12, 13 in spaced relation to one another on its bar 11 extending parallel to the foot 9 and likewise two radiation emitters 15, 16 on its transverse bar 14 adjoining the bar 11. These radiation emitters may, for example, be infrared diodes or ultrasonic emitters. The attachment member 10 may be releasably placed on the foot 9 but can, however, be placed relative to the foot 9 only in a quite specific position so that even after the removal and after the replacement of such an attachment member 10 the radiation emitters 12, 13, 15, 16 take up exactly the same position relative to the bone as before the removal.

Marking elements 17 and 18 of this type are secured not only to the thigh 5 and to the lower leg 6 but also to the hip bone 19 and to the ankle bone 20.

Three receiver devices 22, 23, 24, which receive the radiation emitted from the radiation emitters 12, 13, 15, 16, are arranged in spaced relation to one another on a console 21. When radiation is received, the receiver devices generate electrical signals which are supplied to a data processing system 25. On account of the different orientations of marking elements and receiver devices, transit-time differences result between emission and reception of the radiation, and on account of these transit-time differences the data processing system 25 can completely determine for each marking element 7, 8, 17, 18 its position in the space and store these position data. It is, as a result, possible to generate in the data processing system sets of data which correspond to the position of the marking elements and thus to the bones securely connected to them at specific times.

The receiver devices 22, 23, 24 may be of different designs; they may, as described, establish the orientation of the marking elements due to transit-time differences but it would also, in principle, be possible to determine the orientation by way of geometrical measurement of the beam direction of radiation which is emitted by the radiation emitters 12, 13, 15, 16. In other configurations, marking elements can also be used which have no radiation emitters but rather reflection surfaces, at which radiation emitted from the receiver device is reflected. These reflection surfaces can have, for example, a spherical shape.

It is merely essential that it is possible on account of the use of several receiver devices and several emitters or reflection surfaces on the marking elements to clearly determine the position of each marking element in the space.

When two bones are moved relative to one another, this movement can be converted by the data processing system 25 into corresponding sets of data which determine the paths of the marking elements and, thus, of the bones during the movement. The data processing system can determine from these paths points which remain unmoved during such a movement of two bones relative to a joint or move only minimally; these points are designated as points of maximum invariance and defined as articular points of the corresponding joints.

In the case of the hip joint, such an articular point results automatically as central point of the hip joint designed as a ball joint; in the case of the ankle joint such an articular point results as an intersection point of the pivot axes of the ankle joint about an axis extending transversely to the leg and about an axis extending longitudinally in relation to the leg; in the case of the knee joint the situation is more complicated since the knee joint is neither a ball joint nor a hinge joint. During the bending of the knee and during the rotation of the lower leg about its longitudinal axis curves result, on which the points of maximum invariance are located, i.e. essentially curves of maximum invariance, and these converge on one another to a considerable degree. The point of maximum convergence of these curves may be defined as articular point which may be found during the described movement of the thigh bone in relation to the lower leg bone. Such a calculation is also carried out by the data processing system 25 and so, in this way, the data processing system can determine articular points of this type not only in the area of the ankle joint but also in the area of the hip joint and, finally, also in the area of the knee joint.

Furthermore, the data processing system 25 calculates a characteristic direction for the lower leg which results from a straight-line connection of the articular point in the knee and the articular point in the ankle joint; a characteristic direction is determined for the thigh in the same manner and this results from the straight-line connection of the articular point in the knee and the articular point in the hip. These characteristic directions need not necessarily coincide with the actual course of the bone but are virtual directions which result solely from the kinematical data.

Figure 3:
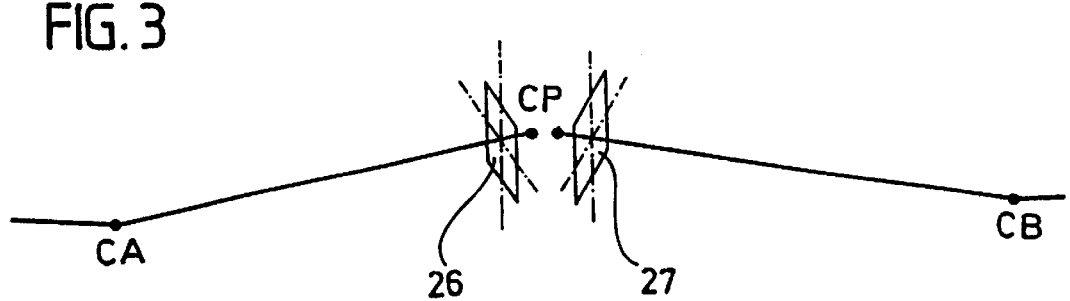
FIG. 3: a schematic view of the characteristic directions of a thigh and a lower leg defined by articular points CA, CP and CB with respective sawing surfaces.

In FIG. 3, the path of these characteristic directions is illustrated schematically. For the thigh, this results from the straight-line connection of the articular point CA close to the hip and the articular point CP close to the knee, for the lower leg due to the straight-line connection of the articular point CB close to the foot and the articular point CP close to the knee.

On the basis of these two characteristic directions obtained solely as a result of movement of the leg of the patient it is possible to determine preoperatively the orientation of a sawing plane, along which the thigh and the lower leg, respectively, have to be cut off in order to implant the prosthetic parts abutting on this sawing surface.

The data processing system determines from the characteristic directions thus obtained the orientation of these sawing planes 26, 27 which are preferably at right angles to the characteristic directions. This is indicated schematically in FIG. 3. The orientation of the sawing planes is thereby calculated relative to the orientation of the marking elements 7 and 8 which, again, are representative for the orientation of the thigh 5 and the lower leg 6.

Figure 4:
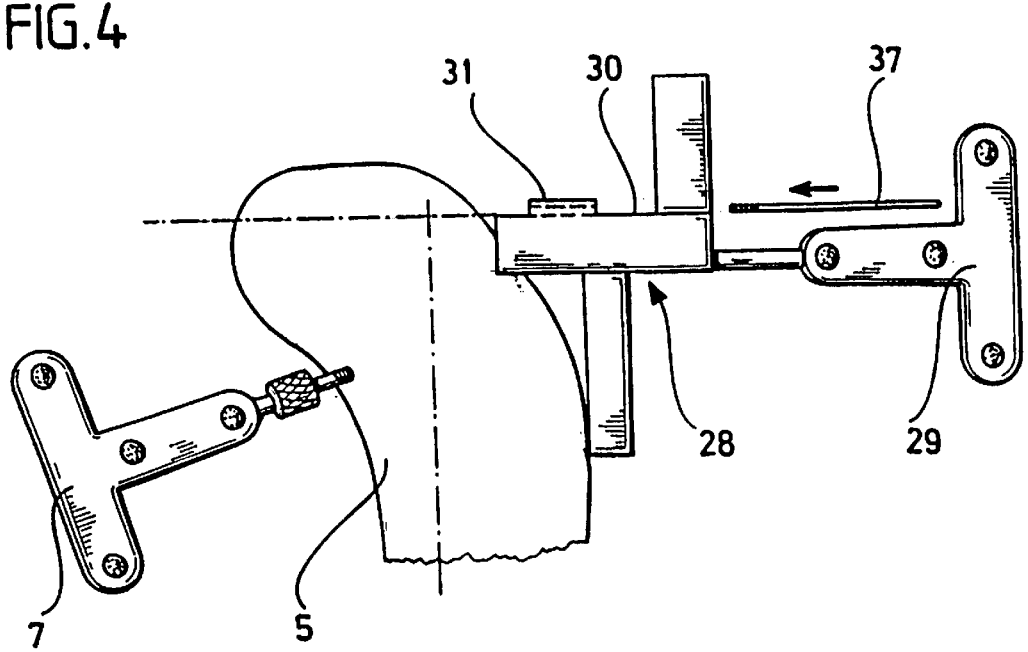
FIG. 4 a schematic view of a bone provided with a marking element with a sawing jig likewise provided with a marking element.

To prepare for the operation, the data of the sawing plane obtained in this manner can now be used to, for example, align a sawing jig 28 relative to a bone. In FIG. 4, this is illustrated schematically on the basis of the thigh bone 5. The thigh bone 5 bears the marking element 7 and so its position in the space can be ascertained in the manner described.

A sawing jig 28 likewise bears a marking element 29 and so the position of the sawing jig 28 in the space can also be determined at any time via the data processing system 25. The sawing jig 28 has a flat guide surface 30 for a saw blade 31; the position of the guide surface 30 relative to the marking element 29 may be determined in a simple manner in that the guide surface 30 is imaged with a calibrated, hand-guided scanning element. For this purpose, this scanning element is guided along the guide surface 30 with its tip; a marking element connected to the scanning instrument thereby reports all the positioning data of the scanning element to the data processing system which can in this manner record the data of the surface, over which the tip of the scanning element travels. After such a calibration, the data processing system has the data available to calculate the orientation of the guide surface 30 from the orientation of the marking element 29.

For the correct orientation of the sawing jig 28 the guide surface 30 must now be oriented such that it is at right angles to the characteristic direction of the thigh bone, and this may be accomplished relatively easily by a difference signal being generated by the data processing system 25 which corresponds to the deviation of the orientation of the guide surface 30 from the orientation of the calculated sawing plane 26. Such a difference signal can be made perceivable for the surgeon in various ways.

Figure 5:
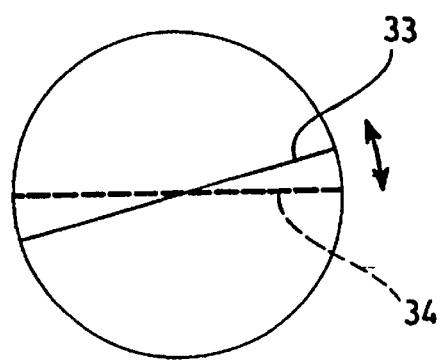
FIG. 5: a diagrammatic illustration of an orientation aid for a tool jig.

For this purpose, a monitor 32 is, for example, arranged on the console 21 and graphic representations, which are a measure for this difference signal, are imaged on it. A possible difference signal can, for example, be reproduced by way of the inclination of two straight lines 33, 34 in relation to one another (FIG. 5), wherein the angle of inclination of the two lines corresponds preferably to the angle of deviation of the sawing plane 26 from the guide surface 30 in one direction. As soon as the guide surface 30 is oriented such that the two intersecting lines 33 and 34 are congruent, the guide surface is oriented as desired in the corresponding direction.

Figure 6:
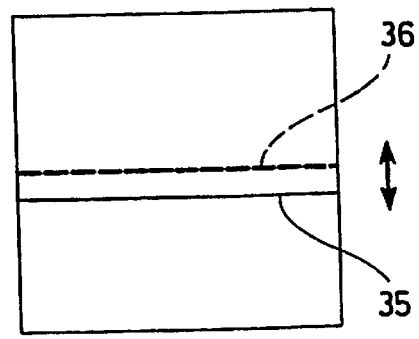
FIG. 6: another embodiment of a diagrammatic orientation aid for a tool jig.

In another graphic representational possibility, the difference signal is represented by the distance between two parallel lines 35, 36 (FIG. 6). When these two lines 35, 36 are congruent, a difference signal no longer exists since guide surface 30 and sawing plane 26 are then oriented as desired in the corresponding direction. In this respect, it is advantageous when the indication according to FIG. 5 and the indication according to FIG. 6 are combined; the indication according to FIG. 5 and the indication according to FIG. 6 then indicate the inclination of the sawing plane 26 relative to the guide surface 30 in directions at right angles to one another. When the difference signal has disappeared in the two representations arranged next to one another, the sawing jig 28 is oriented as desired; this orientation can then be fixed, for example, by means of guide pins 37 driven in.

The manual orientation of the sawing jig 28 as described can, of course, be carried out in another embodiment of the invention by a robot which is controlled by the data processing system 25 in accordance with the sets of data available in it such that the guide surface 30 extends parallel to the sawing plane 26.

The preparation of the operation is thus concluded; the surgeon can now cut off the bones with the desired orientation by guiding the saw blade 31 along the guide surface 30 so that, as a result, a contact surface for a prosthetic part not illustrated in the drawings results. This prosthetic part takes up the desired orientation relative to the bone when abutting on this contact surface and so, in this way, a very exact positioning of prosthetic parts on the bone is possible.

In principle, it would, of course, also be possible for the saw cut itself to be carried out by the robot, wherein this is likewise controlled by the sets of data which are generated and available in the data processing system 25.

The procedure is the same for both the bones adjoining the joint to be replaced and so both prosthetic parts can be position in the desired manner. It is ensured as a result that after the fitting of the prosthetic parts the bones take up the desired orientation, for example, such that the characteristic directions of both bones form a continuous, straight line when the leg is straightened.

What is claimed is:

1. A device for the preoperative determination of positioning data of endoprosthetic parts of a central joint relative to two bones forming the central joint with marking elements securable to the bones, comprising:

a measuring device for determining the position of the marking elements in a space;

a data processing system adapted to receive signals corresponding to positioning data of the marking elements from the measuring device;

at least one marking element being provided for each of the two bones forming the central joint as well as for each of the two bones adjoining these and connected to them via an outer joint;

said data processing system being responsive to the signals during movement of the bones about the two outer joints to determine the points of greatest invariance as outer articular points; and the data processing system determining a characteristic direction for each of the bones from the positioning of the outer articular points and the position of an inner articular point of the two bones forming the central joint.

2. A device as defined in claim 1, wherein the data processing system additionally determines the point of greatest invariance as the articular point of the central joint from the signals during the movement of the bones about the central joint.

3. A device as defined in claim 1, wherein a scanning instrument is associated with the data processing system for supplying signals corresponding to its positioning to the data processing system.

4. A device as defined in claim 3, wherein the data processing system generates a set of data describing the course of the joint surface from a plurality of signals generated by application of the scanning instrument to a joint surface of the bone adjoining the central joint.

5. A device as defined in claim 1, wherein the data processing system determines sawing planes for the orientation of the endoprosthetic parts, said sawing planes serving as contact surfaces for the endoprosthetic parts and taking up a predetermined orientation relative to the characteristic direction.

6. A device as defined in claim 5, wherein the sawing planes are at right angles to the characteristic direction.

7. A device as defined in claim 5, wherein the sawing planes are arranged at a specific distance from the articular point at the central joint determined for the respective bone.

8. A device as defined in claim 1, further comprising a drive device for moving the bones relative to the outer joints and, where applicable, for the movement relative to the central joint.

9. A device as defined in claim 1, wherein the marking elements and the measuring device comprise one of radiation emitters and reflecting surfaces, and a radiation receiver, respectively.

10. A device as defined in claim 1, further comprising a robot, said robot aligning at least one of a tool jig and a tool relative to the characteristic direction.

11. A device as defined in claim 1, wherein a marking element with an orientation determined by the measuring device is associated with at least one of a tool and a tool jig, so that signals corresponding to this orientation are transferred to the data processing system.

12. A device as defined in claim 11, wherein the data processing system determines the orientation of the tool or the tool jig relative to the characteristic direction.

13. A device as defined in claim 11, wherein:

the data processing system generates difference signals for observing the deviation in the orientation of the sawing jig in relation to the characteristic direction, said signals being minimal with a correct orientation, and said data processing system indicating the difference signals optically or acoustically.

14. A device as defined in claim 13, wherein the difference signals are indicated by way of lines inclined relative to one another, said lines extending parallel to one another with a correct orientation.

15. A device as defined in claim 14, wherein the lines intersect.

16. A device as defined in claim 13, wherein the difference signals are indicated by means of the distance between two parallel lines, the distance between said lines disappearing with a correct orientation.

17. A device as defined in claim 13, wherein the difference signals are represented by tones with at least one of a varying loudness and frequency.

18. A device as defined in claim 13, wherein two separate difference signals are generated for angular deviations in planes extending at right angles to one another.

19. A process for the preoperative determination of positioning data of endoprosthetic parts of a central joint relative to a first set of two bones forming the central joint, comprising the steps of:
   moving, relative to one another, a second set of two bones coming together at a first outer joint and having a first bone from the first set of bones, located at an end of the first bone facing away from the central joint, to determine a first articular point for said first bone;
   determining a second articular point in the area of the central joint for said first bone;
   determining a first characteristic direction for said first bone by way of a straight-line connection of the first and second articular points; and
   determining an orientation of the endoprosthetic parts relative to the first characteristic direction.

20. A method in accordance with claim 19, comprising the further steps of:
   moving, relative to one another, a third set of two bones coming together at a second outer joint and having a second bone from the first set of bones, located at an end of the second bone facing away from the central joint, to determine a third articular point for said second bone;
   determining a fourth articular point in the area of the central joint for said second bone;
   determining a second characteristic direction for said second bone by way of a straight-line connection of the third and fourth articular points; and
   determining the orientation of the endoprosthetic parts relative to the first and second characteristic directions.

21. A method in accordance with claim 20, comprising the further steps of:
   securely connecting the second set of two bones and the third set of two bones to marking elements for determining the first and third articular points; and
   determining the respective positions of the marking elements by a measuring device generating signals corresponding to the respective positions and supplying the signals to a data processing system.

22. A method in accordance with claim 19, wherein said second articular point is determined by way of movement, relative to one another, of the first set of two bones forming the central joint.

23. A method in accordance with claim 19, wherein the articular points are established by way of palpatation of the joint surfaces.

24. A method in accordance with claim 19, wherein the articular points are determined with a set of data reproducing the contour of the joint surface at the central joint.

25. A method in accordance with claim 24, wherein the set of data of the contour of the joint surface is determined by scanning the joint surface and storing a plurality of positioning data of points on the joint surface.

26. A method in accordance with claim 19, wherein for the orientation of the endoprosthetic parts, sawing planes serving as contact surfaces for the endoprosthetic parts are determined, said planes taking up predetermined orientation relative to the characteristic direction.

27. A method in accordance with claim 26, wherein the sawing planes are at right angles to the characteristic direction.

28. A method in accordance with claim 26, wherein the sawing planes are arranged at a specific distance from the second articular point.

29. A method in accordance with claim 19, wherein movement of the bones for determining the articular points is carried out by means of a drive device.

30. A method in accordance with claim 19, comprising the further steps of:
   securely connecting the second set of two bones to marking elements for determining the first articular point; and
   determining the respective positions of the marking elements by a measuring device generating signals corresponding to the respective positions and supplying the signals to a data processing system.

31. A method in accordance with claim 30, wherein:
   the marking elements comprise one of radiation emitters and reflecting surfaces; and
   the measuring device comprises several radiation receivers.

32. A method in accordance with claim 30, wherein the point of greatest invariance during the movement of the two bones forming each joint is determined as the articular point for each joint.

33. A method in accordance with claim 19, wherein a sawing jig is aligned relative to the first characteristic direction of the bone for marking a sawing plane.

34. A method in accordance with claim 33, wherein the alignment is carried out by means of a robot.

35. A method in accordance with claim 33, wherein the alignment is carried out manually and the orientation of the sawing jig relative to the first characteristic direction is thereby continuously determined as a result of measurement of the orientation of said jig.

36. A method in accordance with claim 35, wherein:
   difference signals are generated for observing deviation of the orientation of the sawing jig in relation to the first characteristic direction; and
   said difference signals are minimal with a correct orientation and are indicated optically or acoustically.

37. A method in accordance with claim 36, wherein the difference signals are indicated by means of lines inclined relative to one another, said lines extending parallel to one another with a correct orientation.

38. A method in accordance with claim 37, wherein the lines intersect.

39. A method in accordance with claim 36, wherein the difference signals are indicated by means of the distance between two parallel lines, the distance between said lines disappearing with a correct orientation.

40. A method in accordance with claim 36, wherein the difference signals are represented by tones having at least one of varying loudness and varying frequency.

41. A method in accordance with claim 36, wherein two separate difference signals are generated for angular deviations in planes extending at right angles to one another.

42. A method in accordance with claim 19, wherein the positioning data determined on the basis of the first characteristic direction is used to control a machining robot.

43. A device for the preoperative determination of positioning data of endoprosthetic parts of a central joint relative to a first set of two bones forming the central joint, comprising:

at least one marking element securable to each bone from a second set of two bones forming a first outer joint, said second set of two bones having a first bone from the first set of two bones;

a measuring device for determining the position of the marking elements in space;

a data processing system adapted to receive signals corresponding to positioning data of the marking elements from the measuring device; and said data processing system is responsive to the signals during movement of the second set of bones about the first outer joint to determine the point of greatest invariance at the first outer joint as a first articular point;

wherein:

a second articular point is determined in the area of the central joint for said first bone; and a first characteristic direction is determined for the first bone from the position of the first articular point and the second articular point.

44. A device in accordance with claim 43, further comprising:

at least one marking element securable to each bone from a third set of two bones forming a second outer joint, said third set of two bones having a second bone from the first set of two bones; and said data processing system is responsive to the signals during the movement of the third set of bones about the second outer joint to determine the point of greatest invariance at the second outer joint as a third articular point;

wherein:

a fourth articular point is determined in the area of the central joint for said second bone; and a second characteristic direction is determined for the second bone from the position of the third articular point and the fourth articular point.

45. A device in accordance with claim 43, wherein a scanning instrument is associated with the data processing system for supplying signals corresponding to its positioning to the data processing system.

46. A device in accordance with claim 45, wherein the data processing system generates a set of data describing the course of the joint surface from a plurality of signals generated by application of the scanning instrument to a joint surface of at least one of the bones adjoining the central joint.

47. A device in accordance with claim 43, wherein the data processing system determines sawing planes for the orientation of the endoprosthetic parts, said sawing planes serving as contact surfaces for endoprosthetic parts and taking up a predetermined orientation relative to the characteristic direction.

48. A device in accordance with claim 47, wherein the sawing planes are at right angles to the characteristic direction.

49. A device in accordance with claim 47, wherein the sawing planes are arranged at a specific distance from the second articular point.

50. A device in accordance with claim 43, further comprising a drive device for moving bones relative to respective joints.

51. A device in accordance with claim 43, wherein:

the marking elements comprise one of radiation emitters and reflecting surfaces; and the measuring device comprises several radiation receivers.

52. A device in accordance with claim 43, further comprising a robot, said robot aligning at least one of a tool jig and a tool relative to the characteristic direction.

53. A device in accordance with claim 43, wherein a marking element with an orientation determined by the measuring device is associated with at least one of a tool and a tool jig, so that signals corresponding to the orientation are transferred to the data processing system.

54. A device in accordance with claim 53, wherein the data processing system determines the orientation of the tool or the tool jig relative to the characteristic direction.

55. A device in accordance with claim 53, wherein:

the data processing system generates difference signals for observing deviation in the orientation of the sawing jig in relation to the characteristic direction;

the data processing system indicating the difference signals optically or acoustically; and said signals are minimal with a correct orientation.

56. A device in accordance with claim 55, wherein the difference signals are indicated by way of lines inclined relative to one another, said lines extending parallel to one another with a correct orientation.

57. A device in accordance with claim 56, wherein said lines intersect.

58. A device in accordance with claim 55, wherein the difference signals are indicated by means of the distance between two parallel lines, the distance between said lines disappearing with a correct orientation.

59. A device in accordance with claim 55, wherein the difference signals are represented by tones having at least one of varying loudness and varying frequency.

60. A device in accordance with claim 55, wherein two separate difference signals are generated for angular deviations in planes extending at right angles to one another.

* * * * *